US012594284B2

(12) United States Patent
Dattilo

(10) Patent No.: US 12,594,284 B2
(45) Date of Patent: Apr. 7, 2026

(54) COMBINATION OF MICRONUTRIENTS TO STIMULATE THE ENDOGENOUS PRODUCTION OF HYDROGEN SULFIDE (H2S)

(71) Applicant: PARTHENOGEN SAGL, Lugano (CH)

(72) Inventor: Maurizio Dattilo, Montagnola (CH)

(73) Assignee: PARTHENOGEN SAGL, Lugano (CH)

( * ) Notice: Subject to any disclaimer, the term of this patent is extended or adjusted under 35 U.S.C. 154(b) by 704 days.

(21) Appl. No.: 17/996,606

(22) PCT Filed: May 3, 2021

(86) PCT No.: PCT/EP2021/061509
§ 371 (c)(1),
(2) Date: Oct. 19, 2022

(87) PCT Pub. No.: WO2021/224153
PCT Pub. Date: Nov. 11, 2021

(65) Prior Publication Data
US 2023/0172954 A1     Jun. 8, 2023

(30) Foreign Application Priority Data
May 4, 2020     (IT) ........................ 102020000009700

(51) Int. Cl.
| | |
|---|---|
| *A61K 31/675* | (2006.01) |
| *A61K 9/00* | (2006.01) |
| *A61K 9/20* | (2006.01) |
| *A61K 31/145* | (2006.01) |
| *A61K 31/198* | (2006.01) |
| *A61K 31/4415* | (2006.01) |
| *A61P 3/10* | (2006.01) |
| *A61P 9/12* | (2006.01) |
| *A61P 9/14* | (2006.01) |
| *A61P 15/08* | (2006.01) |
| *A61P 25/28* | (2006.01) |
| *A61P 37/06* | (2006.01) |

(52) U.S. Cl.
CPC .......... *A61K 31/675* (2013.01); *A61K 9/0053* (2013.01); *A61K 9/2009* (2013.01); *A61K 9/2013* (2013.01); *A61K 9/2054* (2013.01); *A61K 31/145* (2013.01); *A61K 31/198* (2013.01); *A61K 31/4415* (2013.01); *A61P 3/10* (2018.01); *A61P 9/12* (2018.01); *A61P 9/14* (2018.01); *A61P 15/08* (2018.01); *A61P 25/28* (2018.01); *A61P 37/06* (2018.01)

(58) Field of Classification Search
CPC .. A61K 31/198; A61K 31/675; A61K 31/145; A61K 31/185
See application file for complete search history.

(56) References Cited

U.S. PATENT DOCUMENTS

| | | | |
|---|---|---|---|
| 6,964,969 B2 | 11/2005 | McCleary | |
| 7,972,633 B2 * | 7/2011 | Smith ..................... | A23L 33/10 |
| | | | 514/904 |
| 2007/0166400 A1 | 7/2007 | Rath et al. | |
| 2007/0286909 A1 | 12/2007 | Smith et al. | |
| 2007/0292536 A1 | 12/2007 | Kellermann | |
| 2013/0196429 A1 | 8/2013 | Ali | |
| 2013/0253051 A1 | 9/2013 | Xian et al. | |
| 2014/0178987 A1 | 6/2014 | Liu et al. | |
| 2015/0342969 A1 | 12/2015 | Casola et al. | |
| 2016/0058779 A1 | 3/2016 | Casola et al. | |
| 2017/0216323 A1 | 8/2017 | Casola et al. | |

FOREIGN PATENT DOCUMENTS

| | | |
|---|---|---|
| CN | 102078327 A | 6/2011 |
| CN | 103622992 A | 3/2014 |
| CN | 106243035 A | 12/2016 |
| CN | 106432123 A | 2/2017 |
| DE | 20207569 U1 | 12/2002 |

(Continued)

OTHER PUBLICATIONS

International Search Report dated Jul. 6, 2021 for related PCT Patent Application No. PCT/EP2021/061509, filed May 3, 2021.
"Handbook of Pharmaceutical Excipients Sixth Edition", Pharmaceutical Press; 917 pages; 2009.
Bazhnov, Nikolay, et al., "Thiol-Activated Hydrogen Sulfide Donors Antiviral and Anti-Inflammatory Activity in Respiratory Syncytial Virus Infection", Viruses 2018, 10, 249; doi:10.3390/v10050249; www.mdpi.com/journal/viruses; pp. 1-12.
Bilska-Wilkosz, Anna, et al., "The Role of Hemoproteins: Hemoglobin, Myoglobin and Neuroglobin in Endogenous Thiosulfate Production Processes", International Journal of Molecular Science 2017, 18, 1315; doi:10.3390/ijms18061315; www.mdpi.com/journal/ijms; pp. 1-10.

(Continued)

*Primary Examiner* — Kevin E Weddington
(74) *Attorney, Agent, or Firm* — Perkins Coie LLP; Viola T. Kung

(57) ABSTRACT

The present invention relates to pharmaceutical, dietary and/or food compositions exerting the ability to activate the endogenous production of hydrogen sulfide ($H_2S$) so to feed the redox buffer capacity and to boost the natural ability to compensate both oxidative and reductive stress.
The invention further relates to the use of the aforementioned compositions to correct signs of metabolic derangements such as: oxy-redox imbalances including reductive stress, mitochondrial dysfunction and bioenergetics, insulin resistance, endothelial dysfunction and hyperhomocysteinemia. Accordingly, the composition of the present invention can be used as a medicament for the treatment of hypertension, atherosclerosis and cardiovascular disease, erectile dysfunction, viral infections and inflammatory lung injuries, diabetes and PCOS, autoimmune diseases, neurodegeneration, repeated implantation failure and repeated miscarriage and infertility in both men and women.

5 Claims, No Drawings

(56) References Cited

FOREIGN PATENT DOCUMENTS

| DE | 202006013518 | U1 | 3/2007 |
|----|--------------|-----|--------|
| DE | 202018101715 | U1 | 5/2018 |
| IN | 1334CH2007 | A | 2/2009 |
| WO | 0243507 | A2 | 6/2002 |
| WO | 2005072749 | A1 | 8/2005 |
| WO | 2007070454 | A2 | 6/2007 |
| WO | 2007073175 | A2 | 6/2007 |
| WO | 2012075242 | A2 | 6/2012 |
| WO | 2014094386 | A1 | 6/2014 |

OTHER PUBLICATIONS

Hu, Li-Fang, et al., "Neuroprotective effects of hydrogen sulfide on Parkinson's disease rat models", Aging Cell 2010; Doi: 10.1111/j.1474-9726.2009.00543.x; pp. 134-146.

Kabil, Omer, et al., "Heme-dependent Metabolite Switching Regulates H2S Synthesis in Response to Endoplasmic Reticulum (ER) Stress*", The Journal of Biological Chemistry vol. 291, No. 32, pp. 16418-16423, Aug. 5, 2016 by The American Society for Biochemistry and Molecular Biology, Inc., 6 pages.

Li, Hui, et al., "Role of Hydrogen Sulfide in Paramyxovirus Infections", Journal of Virology; vol. 89, No. 10; pp. 5557-5568; 2015.

Shiraishi, K., et al., "Increased expression of Leydig cell haem oxygenase-1 preserves spermatogenesis in varicocele", Human Reproduction vol. 20, No. 9 pp. 2608-2613, 2005.

Stahl, P. Heinrich, et al., "Handbook of Pharmaceutical Salts Properties, Selection, and Use", International Union of Pure and Applied Chemistry (IUPAC); 13 pages; 2008.

Sun, Qianqian, et al., "Taurine Supplementation Lowers Blood Pressure and Improves Vascular Function in Prehypertension", Randomized, Double-Blind, Placebo-Controlled Study; 2016; 9 pages.

Vandini, Eleonora, et al., "Mechanisms of Hydrogen Sulfide against the Progression of Severe Alzheimer's Disease in Transgenic Mice at Different Ages", Pharmacology; Italy; 11 pages; 2018.

Wang, Jing, et al., "Hydrogen Sulfide as a Potential Target in Preventing Spermatogenic Failure and Testicular Dysfunction", Antioxidants & Redox Signaling, vol. 28, No. 16; 2 pages; 2018.

Kiao, Wusheng, et al., "Metabolic Responses to Reductive Stress", Antioxidants & Redox Signaling; vol. 00, No. 00, 2020.

Yang, Ruili, et al., "Hydrogen Sulfide Promotes Tet1- and Tet2-Mediated Foxp3 Demethylation to Drive Regulatory T Cell Differentiation and Maintain Immune Homeostasis", Immunity 43, 251-263; 2015.

Zanardo, Renata C. O., et al., "Hydrogen sulfide is an endogenous modulator of leukocyte-mediated Inflammation", The FASEB Journal; pp. 2118-2120; 2006.

Dattilo, Maurizio, et al. "Modulation of Human Hydrogen Sulfide Metabolism by Micronutrients, Preliminary Data", Nutrition and Metabolic Insights; vol. 15: 1-13; 2022.

* cited by examiner

COMBINATION OF MICRONUTRIENTS TO STIMULATE THE ENDOGENOUS PRODUCTION OF HYDROGEN SULFIDE (H2S)

The present invention relates to pharmaceutical, dietary and/or food compositions exerting the ability to activate the endogenous production of hydrogen sulfide ($H_2S$) so to feed the redox buffer capacity and to boost the natural ability to compensate both oxidative and reductive stress.

The invention further relates to the use of the aforementioned compositions to correct signs of metabolic derangements such as: oxy-redox imbalances including reductive stress, mitochondrial dysfunction and bioenergetics, insulin resistance, endothelial dysfunction and hyperhomocysteinemia. Accordingly, the composition of the present invention can be used as a medicament for the treatment of hypertension, atherosclerosis and cardiovascular disease, erectile dysfunction, viral infections and inflammatory lung injuries, diabetes and PCOS, autoimmune diseases, neurodegeneration, repeated implantation failure and repeated miscarriage and infertility in both men and women.

BACKGROUND

Hydrogen sulfide ($H_2S$) is, besides nitric oxide (NO) and carbon monoxide (CO), the last discovered among the gasotransmitters regulating many aspects of cells homeostasis. The three gasotransmitters interact each other by synergizing or antagonizing the respective actions in a time and district specific manner whose regulation is still escaping our full understanding.

Endogenous production of $H_2S$ occurs in all living organisms including plants and animals In mammalians $H_2S$ is produced by 3 enzymes: Cystathionine Beta Synthase (CBS) and Cystathionine γ-Lyase (CSE), both requiring pytidoxal-5-phosphate (vitamin B6) as cofactor and both belonging to the transulfuration pathway and responsible for most of the H2S release, and; 3-Mercaptopyruvate SulfurTransferase (3-MST), which is supposed to work mainly in mitochondria and whose activity is less understood. CBS is the enzyme responsible for the first reaction of the transulfuration pathway and catalyzes the conversion of homocysteine and L-serine into L-cystathionine (β-Replacement). CSE is responsible for the following step, the generation of L-cysteine from cystathionine (α,γ-Elimination). The formers are considered the canonical reactions of CBS and CSE, which however exert a particular unspecific recognition of their substrate and can also catalyze alternative reactions leading to the release of $H_2S$.

Alternative reactions releasing $H_2S$ for CBS are:

Cysteine+H2O=serine+$H_2S$ (β-Elimination)

Cysteine+cysteine=lanthionine +$H_2S$ (β-Elimination)

Homocysteine+cysteine=Cystathionine+$H_2S$ (β-/γ-Replacement)

Alternative reactions releasing $H_2S$ for CSE are:

Cysteine+H2O=pyruvate+$NH_3$+$H_2S$ (α,β-Elimination)

Cysteine+cysteine=lanthionine+$H_2S$ (β-Elimination)

Homocysteine+cysteine=Cystathionine+$H_2S$ (β-/γ-Replacement)

Homocysteine+homocysteine=Homolanthionine+$H_2S$ (γ-Replacement)

Hydrogen sulfide is detectable in human plasma at concentrations ranging from high nM to low μM and its half-life ranges from seconds to minutes. It is supposed to act as an autocrine and paracrine signal influencing the metabolic activity and the epigenetic regulation of the releasing cell and of a few to a few hundreds of neighboring cells. The actual genetic expression of the two enzymes of concern and its intensity vary according to the specific cell and tissue. The physiologic effects and the critical concentrations may also vary according to the district. Accordingly, plasma levels may provide little information on the actual imbalance of the system in specific districts or at specific time points.

At molecular level $H_2S$ is signaling mainly by modification of protein targets by promoting persulfidation of protein cysteines, which may modify the active sites of enzymes and other protein characteristics. It also interacts with metal centers, i.e. hemes, of circulating globins and of enzymes (including CBS). Within the cellular nucleus, $H_2S$ exerts the ability to modify the genetic expression acting as an epigenetic effector. Finally, $H_2S$ can be used in mitochondria as a source of reducing equivalents to feed the respiratory chain and the production of ATP.

From a chemical point of view, $H_2S$ behaves as a powerful reducing substance (the standard two electron redox potential of $H_2S/S^0$ couple, at pH 7, versus the standard hydrogen electrode, is −0.23 V). Therefore, $H_2S$ is considered as another player of the endogenous antioxidant system together with NADH/NADPH and glutathione (GSH). It is also possible that $H_2S$ acts as a natural antioxidant within mitochondria.

A deficit in $H_2S$ release has been described in many pathological conditions.

Viral Infections $H_2S$ exerts a protective role in paramyxovirus infection with robust data on infections from the Respiratory Syncytial Virus (RSV). It appears to modulate viral replication and inflammatory responses and treatment in vitro with $H_2S$-donors is able to decrease viral activity. Similar results have been shown on other enveloped RNA viruses from Ortho-, Filo-, Flavi- and Bunyavirus families.

US20160058779, US20150342969 and US20170216323 disclose the administration of $H_2S$ donors, including inhalation, for the treatment of human infections from filoviridae, Ebola virus, paramyxovirus and orthomyxovirus.

Atmosphere Particulate Matter (PM) Lung Damage

Atmosphere particulate matter (PM) has a pathogenetic role in the development of chronic obstructive pulmonary disease (COPD) and lung emphysema that is mediated by oxidative stress and activation of inflammasome complex and cell apoptosis. PM 10, i.e. PM sized below 10 microns, has been also shown to favor several airway viral infections by acting as a carrier, driving viruses deeply into the lung, and as a booster, synergizing with the virus in inducing inflammation. In animal models exposure to PM causes lung injury by activating IL1, IL6 and TGF-beta. These effects are exacerbated by antagonists of $H_2S$ release and are corrected by $H_2S$ donors.

Ventilation Induced Lung Injury (VILI)

Besides obvious therapeutic benefits, mechanical ventilation if used for too long time or with unprecise parameters setting may itself cause or aggravate lung injury, which is called ventilator-induced lung injury (VILI). Thus, this therapeutic intervention becomes difficult to sustain exactly in patients that have an increased need. VILI appears to be mediated by endoplasmic reticulum stress and autophagy. In experimental model these effects and the resulting lung injury are reduced by administration of $H_2S$ donors.

Asthma

The $H_2S$ producing enzymes CSE and CBS are well expressed in smooth muscle cells and endothelial cells of pulmonary blood vessels. Experimental animal models demonstrate an abnormal metabolism of $H_2S$ in asthma with deficit of release associated to bronchospasm, airway remodeling and chronic inflammation, which can be improved by $H_2S$ donors. Compared to unaffected subjects, asthma patients have decreased blood levels of $H_2S$ that further drop during asthmatic crisis.

Endothelial Dysfunction $H_2S$, in concert with nitric oxide (NO) and carbon monoxide (CO), is a main player of vasodilation and neo-angiogenesis and is also involved in the regulation of coagulation and platelet activation. All these activities point to a primary involvement of a $H_2S$ deficit in endothelial dysfunction. Accordingly, experimental data confirm the potential benefit from $H_2S$-enhancing strategies in atherosclerosis, in cardiovascular diseases and in erectile dysfunction.

WO2012075242 and US20130253051 disclose the use of an agent for the controlled, sustained release of $H_2S$ for the treatment of human cardiovascular disease, stroke and erectile dysfunction.

Hypertension (Systemic, Pulmonary, Portal)

$H_2S$ is a main player in vasodilation and neo-angiogenesis and is therefore involved in the homeostatic regulation of blood pressure. In experimental models the blockade of CBS/CSE produces increased blood pressure whereas $H_2S$ revert the effect. Deficits of $H_2S$ generation has been described in systemic, pulmonary and portal hypertension.

CN106432123 discloses the use of a combined $H_2S$ and nitric oxide (NO) donor for the treatment of ischemic heart disease and hypertension.

Autoimmune Diseases $H_2S$ is a powerful inducer of T-lymphocytes differentiation as regulatory T cells (Treg), i.e. those lymphocytes having the task to keep inflammatory processes under control so to avoid tissue damages. The generation of $H_2S$ is indeed hampered in many autoimmune diseases including lupus, systemic sclerosis, amyotrophic lateral sclerosis, rheumatoid arthritis and psoriasis. In experimental models, deprivation of $H_2S$ biogenesis facilitates autoimmune diseases whereas the application/administration of $H_2S$-donors leads to improvements.

Neurodegeneration

All the enzymes producing $H_2S$ are expressed in the brain and their activity appears to modulate key functions including oxy-redox balance, neurotransmission and bioenergetics exerting a neuroprotective function. Brain $H_2S$ levels are deeply reduced in Alzheimer disease and in substantia nigra in Parkinson's disease and restoring its level appears to improve these diseases in experimental models. Multiple sclerosis (MS) is often paralleled by increased homocysteine levels driving the attention to a possible deficit of the transulfuration pathway and to the generation of $H_2S$. In mice models of MS the establishment of the disease parallels a drop in $H_2S$ and $H_2S$ treatment reverts several pathogenetic processes opening to treatment options by $H_2S$ donors.

CN106243035 discloses the use of a tacrine-based H2S donor for the treatment of Alzheimer disease. CN102078327 discloses the use of chemical $H_2S$ donors for the treatment of Alzheimer's and Parkinson's diseases.

Diabetes and PCOS

Circulating $H_2S$ is decreased in type 2 diabetes patients and $H_2S$ donors are effective in improving insulin sensitivity in in vitro and animal models. Accordingly, $H_2S$ donors are supposed to be potentially useful in the treatment of conditions related to insulin resistance including diabetes and PolyCystic Ovary Syndrome (PCOS).

CN103622992 discloses the use of hydrogen sulfide and its donor sulfur hydride for treating type II diabetes.

Infertility $H_2S$ exerts a primary role in both men and women reproductive function. In men, the $H_2S$ producing enzyme CSE is localized in Sertoli cells and immature germ cells whereas CBS is expressed in Leydig cells, Sertoli cells and germ cells. $H_2S$ donors appear to increase testosterone secretion. Subfertile and infertile patients, especially asthenospermic patients, exert lower concentration of $H_2S$ in their seminal plasma and decreased expression of CBS in sperm. Supplementation of exogenous $H_2S$ is effective in improving sperm motility in asthenospermic men. In mice models heat stress causes CBS and CSE down-regulation and decreased $H_2S$ in testis. Accordingly, in the varicocele rat model a fall of $H_2S$ follows varicocele induction and anticipates the deterioration of sperm quality, which is reversed by $H_2S$ donors.

In woman CBS is ubiquitously distributed in the ovary with the strongest expression in follicular cells at all stages. Female mice born from CBS-knockout mothers are sterile. Both CBS and CSE are expressed in the female reproductive tract and gestational tissues, including uterus, vaginal, placental and fetal membrane tissues. In vitro models demonstrate a fall of $H_2S$ at time of labor and administration of $H_2S$ has a potential as a tocolytic treatment. Finally, supplementation of culture media with $H_2S$ donors improves the in vitro development of human embryos and $H_2S$ administration might improve implantation and early pregnancy outcomes.

The wide involvement of $H_2S$ in human pathology has triggered research aimed at individuating therapeutic strategies to boost $H_2S$ in clinical diseases. The very first approach was direct inhalation, which has been tested in animal experiments and resulted in increased blood levels of $H_2S$. However, the difficult handling and storage of this inflammable gas and the imprecision of dosing with risk of toxicity make this approach unsuitable for clinical use. In experimental models $H_2S$ delivery to cells, tissues and animals has been achieved by chemical $H_2S$ donors, i.e. $H_2S$ salts, mainly its natrium salt NaHS. Chemical $H_2S$ donors have been also proposed for human use. Naturally occurring donors are also under investigation. These include the garlic derived substances allicin and its metabolites diallyl disulfide (DADS), diallyl sulfide (DAS), and diallyl trisulfide (DATS). More recently pharmacologic $H_2S$ donors entered pre-clinical research and clinical testing including Gy4137, ACS67, ATB-343, ATB-337, or AP67. Finally, $H_2S$ releasing moieties have been conjugated to existing drugs including aspirin, naproxene and PDE5 inhibitors. None of them has been fully validated for clinical use so far.

DEFINITIONS

Unless otherwise defined, all terms of art, notations and other scientific terminology used herein are intended to have the meanings commonly understood by those of skill in the art to which this disclosure pertains. In some cases, terms with commonly understood meanings are defined herein for clarity and/or for ready reference; thus, the inclusion of such definitions herein should not be construed to represent a substantial difference over what is generally understood in the art.

Within the framework of the present description and in the subsequent claims, except where otherwise indicated, all numbers expressing amounts, quantities, percentages, and so forth, are to be understood as being preceded in all instances by the term "about". Also, all ranges of numerical entities include all the possible combinations of the maximum and minimum numerical values and all the possible intermediate ranges therein, in addition to those specifically indicated hereafter.

The term "active form" herein refers to the metabolite form of the inactive prodrug that is metabolized within the body into its active form.

The term "Pharmaceutically acceptable salts or derivatives" herein refers to those salts or derivatives which possess the biological effectiveness and properties of the salified or derivatized compound and which do not produce adverse reactions when administered to a mammal, preferably a human. The pharmaceutically acceptable salts may be inorganic or organic salts; examples of pharmaceutically acceptable salts include but are not limited to: carbonate, hydrochloride, hydrobromide, sulphate, hydrogen sulphate, citrate, maleate, fumarate, trifluoroacetate, 2-naphthalene-sulphonate, and para-toluenesulphonate. Further information on pharmaceutically acceptable salts can be found in Handbook of pharmaceutical salts, P. Stahl, C. Wermuth, WILEY-VCH, 127-133, 2008, herein incorporated by reference. The pharmaceutically acceptable derivatives include the esters, the ethers and the N-oxides.

The term "physiologically acceptable excipient" herein refers to a substance devoid of any pharmacological effect of its own and which does not produce adverse reactions when administered to a mammal, preferably a human. Physiologically acceptable excipients are well known in the art and are disclosed, for instance in the Handbook of Pharmaceutical Excipients, sixth edition 2009, herein incorporated by reference.

The terms "comprising", "having", "including" and "containing" are to be construed as open-ended terms (i.e. meaning "including, but not limited to") and are to be considered as providing support also for terms as "consist essentially of", "consisting essentially of", "consist of" or "consisting of".

The terms "consist essentially of", "consisting essentially of" are to be construed as a semi-closed terms, meaning that no other ingredients which materially affects the basic and novel characteristics of the invention are included (optional excipients may thus be included).

The terms "consists of", "consisting of" are to be construed as a closed term.

The term "vitamin B6" herein refers to a group of vitamers including pyridoxine, pyridoxamine, pyridoxamine 5'-phosphate, pyridoxal 5'-phosphate and the pharmaceutically acceptable salts or derivatives thereof.

The term "pediatric population" herein refers to that part of the population from birth to eighteen years.

The term "supra-physiologic amounts" herein refers to a dose of a natural substance that is larger than that of an equivalent substance normally present in the body The term "simultaneous, separate or sequential administration" herein refers to administration of the first, second and third compounds of the composition of the invention at the same time or in such a manner that the three compounds act in the patient's body at the same time or administration of one compound after the other compounds in such a manner to provide a therapeutic effect. In some embodiments the compounds are taken with a meal. In other embodiments, the compounds are taken after a meal, such as 30 minutes or 60 minutes after a meal. In some embodiments, one compound is administered for a time period followed by administration of the other compounds.

DETAILED DESCRIPTION OF THE INVENTION

The inventor has observed that $H_2S$-donors, whatever the kinetic of release, cannot replicate the physiologic pattern of release of the endogenous substance. Most of the endogenous $H_2S$ is produced by the enzymes CBS and CSE whose canonical activity is instead the generation of cysteines for proteins and GSH synthesis. Alternative reactions of these enzymes leading to the physiologic $H_2S$ release are activated in a district and time specific manner responding to homeostatic signals that are not yet understood. The release of $H_2S$ from any donor, whatever the type, will be generalized and dependent on time of dosing with no response to any homeostatic feedback. Thus, it is predicted to fail to sharply increase $H_2S$ release and signaling where and when physiologically needed while resulting in excess amounts elsewhere. It has been now surprisingly discovered that $H_2S$ can be increased by activating its endogenous production under the regulation of cellular homeostasis.

The present invention relates to a combination intended to increase the endogenous release of $H_2S$ comprising and preferably consisting of;
- a) a cysteine donor
- b) taurine and/or the pharmaceutically acceptable salts thereof
- c) vitamin B6 and/or the pharmaceutically acceptable salts thereof The cysteine donor is preferably in amounts ranging from 40 to 60% by weight, preferably from 45 to 55%, more preferably of about 49%; taurine is preferably in amounts ranging from 40 to 60% by weight, preferably from 45 to 55%, more preferably of about 49%; vitamin B6 is preferably in amounts ranging from 0.1 to 5% by weight, preferably from 1 to 3%, more preferably of about 2%; the percentages are based on the sum of components a), b) and c), which should sum up to 100.

Vitamin B6 is preferably contained in the combination of the invention at supra-physiologic amounts.

The present invention also includes a composition containing the above-disclosed combination together with one or more physiologically acceptable excipients.

Advantageously, the $H_2S$ induction by the combination of the present invention, acting by an endogenous induction and thus responding to the endogenous bio-feedbacks, will generate $H_2S$ specifically at time when and in the district where the aggression occurs and proportionally to the level of aggression.

CBS and CSE have the canonical function of producing cysteine for proteins and GSH synthesis. The same enzymes use their end product, cysteine, as the main substrate for the production of $H_2S$ and the signals changing the activities of these enzymes are not known. The inventor postulated that cysteines are used by CBS and CSE to produce $H_2S$ only when the concentration of intracellular cysteine raises over the physiologic cell level, which is strictly regulated. Cysteine is the least abundant amino acid in dietary proteins and suboptimal assumption is common. Increases of intracellular cysteine may be attempted by assuming cysteine-containing proteins from food or undenatured whey protein isolate or amino acid preparations. More commonly a soluble form of cysteine, N-acetylcysteine (NAC), is used. However, NAC produces uncontrolled increases of cellular cysteine, which may lead to toxicity. The inventor has noted that the physiologic form of cysteine adsorbed by humans from dietary proteins is L-cystine, i.e. a molecule formed by two cysteines linked by a disulfide bridge (Cys-S-Cys). At time of intestinal protein degradation, the cysteines forming the disulfide bridge and stabilizing the proteins structure (Peptide-Cys-S-Cys-Peptide) are hydrolyzed together resulting in L-cystine that is soluble and enters the circulation and thereafter the cells by means of both passive and active transport. Within the cell, L-cystine is cleaved to generate 2 cysteines on demand, i.e. based on metabolic need. Thus, the inventor concluded that L-cystine may be a better effective form to administer cysteine without acutely affecting the level of free cysteine while at the same time creating a cellular reservoir to be used at time of need. The human daily intake of cysteine/cystine is variable according to the feeding pattern, however it can be estimated in the range of 1000 mg per day. Assumption of larger amounts, up to 3 times the above values, may occasionally occur in vegans assuming more of vegetable proteins without causing known metabolic derangements. On this basis it can be established that, in normally feeding subject, the daily assumption of an extra amount of L-cystine as low as 100 mg per day is already enough to produce a metabolic effect as well as a dose of 2000 mg per day remains tolerated. However, in standard subjects, it is expected that a daily dose of 250 to 500 mg, associated to the other micronutrients, may be appropriate to sustain an increased release of $H_2S$.

According to a preferred embodiment of the present invention the cysteine donor is L-cystine or N-acetylcysteine, preferably L-cystine. According to another preferred embodiment of the present invention the daily dose of L-cystine is comprised between 100 and 2000 mg per day, preferably 200 to 1000 mg per day, more preferably between 250 and 500 mg per day.

However, the cellular concentration of cysteine is sharply regulated and any excess is immediately removed by the enzyme cystine di-oxygenase (CDO) forming cysteine sulfinate that is thereafter metabolized to hypotaurine and finally to taurine. CDO is the most inducible enzyme and its expression can rapidly increase up to 40-fold the basal one to efficiently remove any excess of cysteines. Therefore, isolated cysteine administration is predicted to fail to increase $H_2S$ levels and this was also experimentally confirmed by the inventor. It has been now surprisingly discovered that co-administration with L-cystine of taurine, i.e. the end-product of cysteine catabolism by CDO, is effective in lifting up the concentration of free cysteines and to boost biochemical pathways using cysteine. The mechanism is likely a retrograde feedback exercised by the end product taurine on its own biosynthesis so that the increased cysteine concentration does not trigger CDO induction and hyperactivity. Thus, if taurine level grows, the intracellular regulation of free cysteine gets lifted up to a somehow higher level. As a matter of fact, the inventor has noted that co-administration of L-cystine and taurine to humans results in increased generation of lanthionine, which is indeed the product of the CBS reaction releasing $H_2S$. The inventor has assessed the added effect of taurine on L-cystine supplementation and has confirmed that an increased $H_2S$ production compared to L-cystine alone is already measured at a daily dose of 100 mg per day of taurine whereas daily amounts larger than 2000 mg do not produce any further added effect.

According to a preferred embodiment of the present invention the daily dose of taurine is comprised between 100 and 2000 mg per day, preferably 200 to 1000 mg per day, more preferably between 250 and 500 mg per day.

The inventor also noted that the concentration of homolanthionine, i.e. the product of the CSE reaction releasing $H_2S$, had not been raised by the administration of L-cystine and taurine. Thus, the activation of the system was still partial as CSE is believed to be the major endogenous source of $H_2S$ in peripheral tissues.

Both CBS and CSE use vitamin B6 as the necessary co-enzyme. CSE exhibits much greater loss of activity than CBS during B6 insufficiency. However, in subjects with chronically low-vitamin B6 status, plasma concentrations of lanthionine and homolanthionine did not respond to pyridoxine supplementation. The inventor has now surprisingly discovered that the supplementation of supra-physiological amounts of vitamin B6 is effective in activating CSE activity and that it results in CSE reaction augmentation to a larger extent than CBS reactions. Moreover, it was surprisingly discovered that co-administration of supra-physiologic amounts of vitamin B6 together with L-cystine and taurine results in a significant and intra and inter-subject consistent over production of both lanthionine and homolanthionine indicating a complete activation of the $H_2S$ release. The parallel increase of the average plasma concentration of $H_2S$, although of lower biological significance, also confirmed the direction of the metabolic change. The inventor also noted that the administration of standard vitamin B6 (pyridoxin or pyridoxine hydrochloride) failed to trigger the system in some subjects, possibly due to a genetic weakness in the processes of vitamin B6 activation and recycling, and that the same subjects responded normally when activated vitamin B6, namely pyridoxal-5-phosphate (P5P), was administered. The inventor has assessed the added effect of vitamin B6 on taurine and L-cystine supplementation and has confirmed that an increased $H_2S$ production compared to L-cystine and taurine is already measured at a daily dose of 2 mg per day of vitamin B6 whereas daily amounts larger than 100 mg do not produce any further added effect.

According to a preferred embodiment of the present invention the daily dose of vitamin B6 is comprised between 1 and 100 mg per day, preferably 2 to 50 mg per day, more preferably between 5 and 20 mg per day. According to another preferred embodiment of the present invention vitamin B6 is pyridoxal-5-phosphate.

In summary, the inventor has surprisingly found that the supplementation of a combination of micronutrients comprising L-cystine, taurine and supra-physiologic doses of vitamin B6 is effective in inducing the endogenous generation of $H_2S$. According to a first aspect thereof, the present invention relates to a combination intended to increase the endogenous release of $H_2S$ comprising;

a) L-cystine and/or a pharmaceutical acceptable salt thereof in an amount comprised between 100 and 2000 mg per day, preferably 200 to 1000 mg per day, more preferably between 250 and 500 mg per day b) Taurine and/or a pharmaceutical acceptable salt thereof in an amount comprised between 100 and 2000 mg per day, preferably 200 to 1000 mg per day, more preferably between 250 and 500 mg per day c) Pyridoxal-5-phosphate a pharmaceutical acceptable salt thereof in an amount comprised between 1 and 100 mg per day, preferably 2 to 50 mg per day, more preferably between 5 and 20 mg per day Advantageously, L-cystine provides a cellular reservoir of cysteines to be mobilized on demand, thus acting as a buffer for intracellular cysteine concentration.

Advantageously, taurine exerts the ability to decrease cysteine catabolism and to lift up the intracellular regulation of the level of free cysteines that become available for $H_2S$ synthesis.

Advantageously, supra-physiologic doses of pyridoxal-5-phosphate further enhance the activity of CSE toward $H_2S$ producing reactions.

Advantageously, the administration of the already activated form of vitamin B6, pyridoxal-5-phosphate, allows to reach effective vitamin B6 supra-physiologic activity also in subjects carrying genetic weaknesses of the enzymes responsible for B6 activation.

In a preferred embodiment of the present invention the compositions are to be assumed on a daily basis by any systemic route, including but not limited to oral, injective, trans-rectal, intranasal, transdermal and by aerosol or bronchoalveolar lavage. The pharmaceutical, dietary and/or food compositions of the present invention are preferably formulated in solid or liquid form. Said solid form being selected from tablet, capsule, granule, or suppository, more preferably tablet. Said liquid form being selected from soluble granule, drinkable solution, injection or breathable solution.

In a preferred embodiment of the invention, the composition according to the invention comprises the combination of components a), b) and c) and at least one physiologically acceptable excipient.

To obtain the pharmaceutical, dietary and/or food compositions according to the present invention the following classes of known excipients are preferably used: bulking agents (cellulose, calcium phosphate), stabilizers (cross-linked carboxymethyl cellulose), anti-caking agents (mono and di-glycerides of fatty acids, silicon dioxide), sweeteners, surfactants (cationic, anionic or non-ionic), diluents, aggregating agents or binders, lubricants, glidants, solubilizers, emulsifiers, humectants, flavoring agents, coating agents, colorants, acidity regulators, or a mixture thereof. Preferably, bulking agents, anticaking agents, stabilizers and a mixture thereof.

According to a second aspect thereof, the present invention relates to the aforementioned combination and/or compositions for use as medicament.

Advantageously, the combination according to the present invention allows to up-regulate and/or to re-activate the endogenous release of $H_2S$ in subjects with known or suspected, isolated or pathology-associated deficiency of the natural release.

The inventor further noted that the combination of micronutrients also induced an increased concentration of 3-mercaptopyruvate (3MP), pyruvate and sulfates ($SO_4$) and improvements of mitochondrial function with a lower amount of hydrogen peroxide ($H_2O_2$) generated for the same amount of ATP produced. A further pathway for intracellular cysteine metabolism is indeed its conversion to 3MP by cysteine aminotransferase (CAT). In mitochondria 3MP is converted by 3-mercaptopyruvate sulfurtransferase (3MST) to pyruvate and $H_2S$. $H_2S$ can be then further oxidized to $SO_4$ in the mitochondrial respiratory chain contributing to ATP generation. Thus, the increase of 3MP, pyruvate and $SO_4$ after the administration of the micronutrients indicates that the increased cysteine level was also able to stimulate the third, mitochondrial source of $H_2S$, which is a surprising finding.

Advantageously, the combination according to the present invention is used to boost mitochondrial activity by improving the energy output, i.e. to correct mitochondrial dysfunction.

The inventor has also noted that the administration of L-cystine, taurine and B6 in humans, besides increasing the plasma concentration of lanthionine, homolanthionine, 3MP, pyruvate, $SO_4$ and $H_2S$, also induces a lower ratio of NADH to NAD+, of NADPH to NADP+ and of GSH to GSSG with the effect being better evident in subjects starting from an imbalance toward the reduced state and no effect in subjects starting from an imbalance toward the oxidized sate. Thus, the combination of micronutrients promotes a better balance between the redox and the oxidative state of the major regulators of cellular redox homeostasis in favor of their oxidative form and mainly when there is an excessive reducing state. This is surprising because $H_2S$ is a powerful reducing substance and was supposed to add onto cellular antioxidant capacity. Any imbalance between the cellular redox effectors in favor of their reduced form has been defined reductive stress and is shown to cause the generation of oxygen free radical and of oxidative damage to nucleic acid, proteins and lipids of the same type of those caused by oxidative stress (Xiao W & Loscalzo J, Antioxid Redox Signal. 2019; doi: 10.1089/ars.2019.7803). The inventor has now surprisingly discovered that $H_2S$ serves as an escape pathway to dispose of any excess of reducing equivalents generated by both the cytosolic and mitochondrial metabolism. Briefly, excess of reducing equivalents in the form of NADH, NADPH and GSH are transformed into cysteine and then $H_2S$ which is finally oxidized to $SO_4$ generating ATP and final disposal of the sulfur moiety and of the excessive reducing power.

Advantageously, the combination according to the present invention is used to correct reductive stress, whether constitutional or caused by intercurrent illnesses, in humans. Advantageously, the increased release of $H_2S$ will also contribute in the opposite direction, i.e. to compensate an oxidative stress by sparing NADH/NADPH and GSH.

A defective activity of either CBS or CSE is known to result in increased circulating level of homocysteine. This is a non-proteogenic amino acid resulting from de-methylation of methione/S-adenosylmethionine in transmethylation reactions. Homocysteine is the substrate of CBS to produce cystathionine according to the canonical reaction of the enzyme. Several genetic variants of CBS have been linked to the occurrence of homocystinuria, an inherited disorder of the metabolism causing a multi-systemic disorder of the connective tissue, muscles, central nervous system (CNS), and cardiovascular system and shortening of life expectation. Homocystinuria is characterized by very high blood levels and large excretion of homocysteine in urine. Besides CBS deficiency, defective genetic variants of other enzymes including but not limited to CSE and all the enzymes participating to homocysteine re-methylation to methionine are known to cause milder forms of hyperhomocysteinemia, which has been linked with the development of many chronic and degenerative disease. The inventor has noted that the administration of a combination of L-cystine, taurine and supra-physiological doses of vitamin B6 is very effective in lowering blood homocysteine concentration. Surprisingly, the effect of this combination was better effective in correcting the blood homocysteine level than the administration of full doses of methylfolate and methylcobalamin, both being methyl donors contributing to homocysteine re-methylation. More surprisingly, the combination on subject was better effective in reducing homocysteine than methylfolate plus methylcobalamin also in carriers of the known defective variants of methylene tetrahydrofolate reductase (MTHFR), Methionine synthase (MTR), Methionine synthase reductase (MTRR) and choline dehydrogenase (CHDH). Further surprising, the homocysteine lowering effect of the combination was associated to increased blood concentration of methylfolate and methylcobalamine that was larger than that achieved by the administration of the methyl donors. It is therefore postulated that an increased flux of $H_2S$ contributes to the activation of MTHFR and possibly of other enzymes involved in homocysteine re-methylation.

In a preferred embodiment, the combination according to the present invention is used to correct hyperhomocysteinemia, including homocystinuria, whether constitutional or caused by intercurrent illnesses, in humans.

Insulin resistance has been shown to represent an adaptive mechanism to mitochondrial dysfunction. Briefly, intensive bioenergetic activity in mitochondria generates reactive oxygen species (ROS) that may finally kill the mitochondrion. However, excessive ROS can be converted by superoxide dismutase to $H_2O_2$ that freely diffuse out of the mitochondrion and reaches the outer cell membrane. Here $H_2O_2$ oxidizes the insulin receptor that gets blocked. In this way, mitochondria signal to the cell to block the entrance of substrates to avoid final damage. The result is that glycemia and insulinemia increase while the output of ATP remains below the demand, which is called mitochondrial dysfunction. The inventor has surprisingly discovered that the administration of L-cystine, taurine and supra-physiologic doses of vitamin B6 is very effective in reverting insulin resistance is subjects with an evident imbalance, including type 2 diabetes and PCOS patients, although there is no effect in subjects whose glycemic control has no alterations. It is postulated that the increase release of $H_2S$ induced by the micronutrients is able to act as an antioxidant buffer within mitochondria so to avoid the accumulation and export of ROS, hence avoiding the establishment of the compensatory insulin resistance.

In another preferred embodiment, the combination according to the present invention is used to correct insulin resistance and other disturbances of glucose metabolism, including diabetes and PCOS, whether constitutional or caused by intercurrent illnesses, in humans.

Endothelial dysfunction is characterized by imbalanced vasodilation and vasoconstriction, disruption of the endothelial barrier permeability and activation of vascular and peri-vascular inflammation. All of these functions require integrity of $H_2S$ signaling and a deficit in $H_2S$ release and/or activity has been reported in all the diseases linked to endothelial dysfunction. Zanardo et al (FASEB J. 2006; 20(12): 2118-20) described a mechanism in place in the cardiovascular and nervous system explaining how $H_2S$ is protective against inflammation. Briefly, $H_2S$ released by small vessels is able to keep open the $K_{ATP}$ channels of leucocytes decreasing the ability of these cells to adhere to the endothelium and to trigger the inflammatory cascade. $H_2S$ inhibitors increase leucocyte adhesion whereas $H_2S$ donors play as inhibitors. Accordingly, as long as the endothelial release of $H_2S$ is sustained very little inflammation may develop. The involvement of $H_2S$ is well known in the endothelial dysfunction observed in myocardial infarction and reperfusion injury, hearth failure, atherosclerosis and erectile dysfunction. This is leading to the therapeutic potential of $H_2S$ donors in the above diseases, although it is clear that a straight increase is unlikely to properly modulate the homeostatic regulations. In contrast, any boost to the endogenous ability to react by robust $H_2S$ responses has high potential therapeutic value.

In another preferred embodiment, the combination according to the present invention is used to correct endothelial dysfunction associated to clinical diseases, including but not limited to, myocardial infarction and reperfusion injury, hearth failure, atherosclerosis and erectile dysfunction.

$H_2S$ is released by both the endothelium and the smooth muscular fibers of blood vessels to trigger vasodilating responses. These actions are orchestrated in direct dialogue with another gasotransmitter, nitric oxide (NO), and $H_2S$ on one side synergizes with NO in the vasodilation and on the other one scavenges vascular NO and controls its endogenous levels in peripheral arteries. According to experimental models, the inhibition of $H_2S$ release generates systemic hypertension whereas $H_2S$ donors exert a corrective action. Similar findings are also reported for pulmonary hypertension and portal hypertension. Sun Q et al (Hypertension. 2016 Mar; 67(3):541-9) demonstrated that taurine daily administration for 12 weeks significantly decreases the blood pressure of pre-hypertensive patients (diastolic blood pressure between 80 and 89 mm Hg) and that this was associated to an increase of circulating $H_2S$. It must be noted that Sun Q et al (2016) administered a huge amount of taurine (1.6 gr per day), that the reduction of diastolic and systolic blood pressure was of limited extent (respectively 3.4 and 4.6 mm Hg) and that the blood levels of $H_2S$ are of little clinical value. They also showed that taurine had induced the expression of CBS and CSE but did not check the expression of CDO (likely reduced) and the intracellular cysteine level (likely increased) and therefore could not understand that taurine was acting as a CDO inhibitor and that other substances were needed to complete the action. Nevertheless, these data confirm that any boost to the endogenous ability to react by robust $H_2S$ responses has high potential therapeutic value in hypertension.

In another preferred embodiment, the mixture according to the present invention is used to treat hypertension, such as systemic hypertension, pulmonary hypertension and portal hypertension.

$H_2S$ is a key player in the protection of the airway's mucosa against a wide array of pathogenic processes. The action of $H_2S$ on the $K_{ATP}$ channels of leucocytes described by Zanardo et al (FASEB J. 2006; 20(12): 2118-20) is likely involved also in its effects on the airways and modulates the effects of lung injuries, i.e. particulate matter in the atmosphere, ventilation induced lung injury (VILI), asthma, and viral infections. It has been shown that the early pathogenic events in viral airways infection include a depression of the release of $H_2S$ whereas a reactivation of $H_2S$ parallels the healing phase (Li H et al J Virol. 2015; 89(10): 5557-68). Experiments based on the use of inhibitors and donors of $H_2S$ showed that $H_2S$ exerts a protective role in paramyxovirus infection as well as on other enveloped RNA viruses from Ortho-, Filo-, Flavi- and Bunyavirus families (Bazhanov N et al, Sci Rep. 2017; 7: 41029). The airway and lung injury caused by the atmosphere particulate matter is also mediated by a deficiency of $H_2S$. Interestingly, PM 10, i.e. PM sized below 10 microns, has been also shown to favor several airway viral infections. Ventilator-Induced Lung Injury (VILI) occurring in patients undergoing intensive and long-lasting assisted ventilation is as well related to a fall of $H_2S$. Finally, an abnormal metabolism of $H_2S$ is described in asthma with deficit of release associated to bronchospasm, airway remodeling and chronic inflammation and reversion of these findings by $H_2S$ donors. The inventor has surprisingly discovered that the combination subject of the present invention is able to stimulate $H_2S$ also in the human airways, which offers valuable therapeutic uses of the present invention.

In a further aspect, the present invention relates to the use of the aforementioned compositions in the prevention and/or treatment of viral infections, including but not limited to those affecting the airways and the lung and caused by paramyxovirus and other enveloped RNA viruses from Ortho-, Filo-, Flavi- and Bunyavirus families.

It is noted that other pathogenic noxae affecting the lung, i.e. particulate matter, VILI and asthma, also act by an interference with H2S and thereby may generate independent damage and/or synergise with viral infections.

In a further aspect, the present invention relates to the use of the aforementioned compositions in the prevention and/or treatment of airway and lung damages caused by atmosphere particulate matter, including but not limited to those caused by PM 10, and by assisted ventilation.

In a further aspect, the present invention relates to the use of the aforementioned compositions in the prevention and/or treatment of asthma.

Coronaviruses share many characteristics with the RSV including the RNA genome, the presence of an envelope, the recognition of glycoproteic receptors and the mechanism of invasion and establishment of lung lesions. The inventor has surprisingly discovered that also the recent coronavirus outbreak (Covid 19) caused by the virus SARS-cov2 responds to the same $H_2S$-related mechanisms. SARS-cov2 has been shown to interact with the heme-proteins by means of its e ORF8 and surface glycoprotein. This results in dissociation of the iron and interference with the normal heme anabolic pathway). In humans, the enzyme responsible for heme catabolism is heme oxygenase 1 (HO-1) that degrades hemoglobin (and other heme-globins) to ferrous iron ($FE^{++}$), that is incorporated in ferritin, biliverdin and carbon monoxide (CO). CO is the only so far known factor that can trigger the change of substrate specificity of CBS to produce $H_2S$ instead of cysteine/GSH. Indeed, Kabil et al (J Biol Chem 2016; 291(32): 16418-16423) demonstrated that HO-1 expression is triggered by the endothelial reticulum (ER) stress, i.e. protein misfolding due to reductive stress resulting in opening of the disulfide bridges, and that the resulting CO is able to bind CBS to induce a $H_2S$ response. The disruption of heme by SARS cov-2 causes a sharp shortage of the heme substrate for HO-1 and results in a drop of $H_2S$ release at sites of infection. Besides interfering with $H_2S$ generation, the catabolism of hemoglobin and other heme-globins by SARS-cov2 also hampers $H_2S$ signaling, i.e. persulfidation of protein cysteines. Bilska-Wilkosz A et al (Int J Mol Sci 2017; 18: 1315) described the interactions between hydrogen sulfide and hemoglobin, myoglobin and neuroglobin to show that they are a main site of production of thiosulfate from $H_2S$, which is metabolically relevant and likely responsible for many of the biological actions of $H_2S$. Worth to note, the $K_{ATP}$ channels responsible for the $H_2S$- induced inhibition of leucocyte adhesion described by Zanardo et al (2006) are known to be activated by a persulfidation mechanism. Thus, SARS-cov2 interferes with both the release (interference with HO-1) and the signaling (lack of persulfides generation) of $H_2S$ and the Covid 19 disease will benefit from a treatment enhancing $H_2S$ activity.

In a further aspect, the present invention relates to the use of the aforementioned compositions in the prevention and/or treatment of the SARS cov-2 infection and the resulting Covid 19 disease.

All the enzymes generating $H_2S$, CBS, CSE and 3MST are expressed in the brain with CBS expression particularly abundant in astrocytes and 3MST more strongly expressed in the cerebellum. Within the CNS, $H_2S$ is believed to exerts antioxidant and neuroprotective functions and a deficit of $H_2S$ function is involved in several neurodegenerative diseases including, but not limited to, Alzheimer's disease (AD), Parkinson's disease (PD), Hungtington's disease and Amyotrophic lateral sclerosis (ALS). It is noted that all the substances included in the composition subject of the present invention are well represented in the CNS and the same substances reach the CNS after systemic administration.

Advantageously, the combination according to the present invention is used to increase the endogenous release of $H_2S$ in the central nervous system in humans and to improve the outcome of neurodegenerative diseases in humans.

Hu L-F et al (Aging Cell 2010; 9: 135-146) administered a chemical $H_2S$ donor to rats with neurotoxin-induced PD and demonstrated that it prevented neurodegeneration. A similar model in mice showed that inhaled $H_2S$ prevents neurodegeneration and movement disorder. In another preferred embodiment, the combination according to the present invention is used to treat Parkinson's Disease in humans.

The levels of $H_2S$ are severely decreased in the brains of AD patients compared with the brains of the age matched normal individuals. In an AD model in mice, the intraperitoneal administration of a chemical $H_2S$ donor reverted the Aβ-imparted cognitive deficiency by decreasing the generation of Aβ and repressing the downregulation of CBS and 3MST. More recently, Vandini E et al (Pharmacology 2019; 103: 50-60) recorded the positive clinical effect of the administration to AD transgenic mice of both a $H_2S$ donor and sulfur water (rich in $H_2S$) to conclude that appropriate treatments with various sources of $H_2S$, might represent an innovative approach to counteract early and severe AD progression in humans.

In another preferred embodiment, the combination according to the present invention is used to treat Alzheimer's Disease in humans.

Regulatory T cells, or Tregs, behave as a kind of built-in brake of the immune system ensuring that immune and inflammatory responses remain equilibrated without inducing excessive damages. Tregs are known to be poorly functioning in autoimmune patients and the enhancement of Treg function is a best promising approach in the treatment of such diseases. Clinical trials are ongoing to test the efficacy of the infusion of Tregs, either naive or antigen-specific engineered, alone or in combination with immuno-modulators to treat a variety of autoimmune diseases and host versus graft disease. Pending the results, the clinical suitability of this strategy is low due to cost, technology requirement and safety concerns. Moreover, the actual localization and migration of the injected Treg at the desired site of action remains a main and unaddressed challenge. $H_2S$ is the actual metabolic trigger of lymphocyte differentiation toward the Treg type. It activates the DNA de-methylases Tet1 and Tet2 (methylcytosine dioxygenases) to demethylate and activate the Foxp3 regulatory locus, which is followed by Treg differentiation and immune homeostasis (Yang R et al, Immunity 2015; 43: 251-263). $H_2S$ was required for Treg cell differentiation, conversely $H_2S$ deficiency results in decreased Tet1 and Tet2 expression in T cells.

Advantageously, the combination according to the present invention is used to promote the differentiation of Treg lymphocytes in subjects with autoimmune disease or undergoing donor organ transplant.

Treg lymphocytes also have a key role in regulating the formation of cutaneous scars. Keloids and hypertrophic scars are known to carry a lower than expected number of Tregs. The reduction in number and function of Tregs is supposed to cause continuing activity of fibroblasts in synthetizing collagen, although no specific therapeutic intervention has been developed. The inventor has now surprisingly discovered that the oral administration of the combination of the present invention is very effective in reducing the scar activation leading to reduction in keloid size within a few months of treatment.

Advantageously, the combination according to the present invention is used to promote the differentiation of Treg lymphocytes in subjects with hypertrophic scars and keloids.

There is clear evidence that the HO-1/CO system is involved in neuroinflammatory disorders such as Multiple Sclerosis (MS) and CO delivery was proposed as a treatment option. Thereafter, in vitro models proved that therapeutic effect could be achieved by $H_2S$ donors, being indeed $H_2S$ release the final outcome of HO-1/CO activation. It is believed that T lymphocytes play a major role in the initiation and propagation of MS by generating inflammation that stimulates the microglia cells to the destruction of the myelin and lymphocytes to differentiate into B-cells and that a deficit of Treg lymphocytes is involved. The inventor has noted that $H_2S$ is both the result of HO-1/CO activation and the agent inducing Treg differentiation. Therefore, a boost to $H_2S$ release will be of benefit to autoimmune diseases. In another preferred embodiment, the combination according to the present invention is used to treat Multiple sclerosis and to prevent its relapses in humans. Psoriasis is a common T-cell-mediated chronic inflammatory skin disease where genetic predisposition and environmental factors trigger the immune system to develop the lesions. Serum $H_2S$ levels in psoriasis patients are far lower than their controls and the $H_2S$ level inversely correlates with the severity of the disease. Treg dysfunction is clearly demonstrated in psoriasis and was shown to be caused by the activating phosphorylation of STAT3, a latent cytoplasmic transcription factor. The inventor has noted that in animal models the expression of STAT3 is inhibited by $H_2S$ so that increased $H_2S$ generation has the potential to completely revert the pathologic derangement in psoriasis.

In another preferred embodiment, the combination according to the present invention is used to treat psoriasis and to prevent its relapses in humans.

Treg mediated immunotolerance is of paramount importance also for the establishment and maintenance of human pregnancy. HO-1 has been implicated in counteracting the overwhelming inflammatory immune responses towards fetal allo-antigens, thereby contributing to fetal acceptance, which is again driving the attention to the $H_2S$-induced Treg differentiation and activity. In natural human pregnancy the rise in uterine artery blood flow appears consequent to the VEGF-stimulated release of $H_2S$ by increased CBS expression in the endothelium. In the uterine artery, both CBS expression and $H_2S$ release have been demonstrated to be increased in the proliferative phase of non-pregnant women and in pregnant women as compared to the secretory phase of non-pregnant women, which strongly confirms a role in the uterine hemodynamics. Inasmuch, adequate $H_2S$ release is necessary for both the immunotolerance at time of implantation and for the proper development of uterine and placental vascularization allowing the maintenance of the pregnancy and the development of the fetus. $H_2S$ keeps its pregnancy maintenance function up to the very end and at time of labor the fall of $H_2S$ exerts a permissive role. Accordingly, an inappropriate early fall of $H_2S$ may contribute to a pre-term labor and a supportive treatment may prevent it.

In a preferred embodiment, the combination according to the present invention is used to treat recurrent implantation failure and recurrent pregnancy loss in humans, either in natural conception and within Assisted Reproductive Technology (ART) cycles. In another preferred embodiment, the combination according to the present invention is used to treat pre-term labor in women.

An appropriate functioning of the $H_2S$ releasing machinery is essential to the maturation of both male and female gametes and to embryo development. In vitro maturation experiments with porcine oocytes showed that a fall of $H_2S$ characterize the onset of oocyte ageing and that the application of $H_2S$ donors prevents this ageing. Further experiments demonstrated that the antiageing effect is mediated by the ability of $H_2S$ to modulate $K_{ATP}$ and Ca channels. A high expression of the hemoglobin gene was demonstrated in the granulosa and cumulus cells in mice whereas no genes of erythrocyte differentiation were activated, but the authors could not properly explain this finding. When hemoglobin was added to the culture, it localized in the cumulus and diffused to the oocyte only after hCG triggering indicating a hormonal control regulating its role in follicle maturation. In other experiments it was shown that the application of $H_2S$ donors triggered and improved porcine oocyte maturation in vitro. The inventor has now surprisingly discovered that the role of hemoglobin in granulosa cells is to act as a substrate for HO-1, which is well expressed in ovarian follicles, so to enhance the activation of $H_2S$ secretion in response to endocrine signals, and that a constitutional or disease-induced weakness of the HO-1/CO/$H_2S$ axis contributes to idiopathic female infertility as well as to the women infertility associated with PCOS, advanced reproductive age and premature ovarian failure.

In a preferred embodiment, the combination according to the present invention is used to treat women infertility.

In the testes, the $H_2S$ producing CSE is localized in Sertoli cells and immature germ cells whereas CBS is expressed in Leydig cells, Sertoli cells and germ cells. It is pretty clear that $H_2S$, in co-ordination with NO and CO, is a main regulator of testicular and spermatic function, although the specific mechanisms remain elusive. Wang J et al (Antiox & Redox Sign 2018; 28(16): 1447-1462) found that both subfertile and infertile patients, especially asthenospermic patients, exhibited decreased concentration of $H_2S$ in their seminal plasma and diminished expression of $H_2S$-generating enzymes. In other studies, the administration of $H_2S$ donors to oligoasthenospermic men resulted in a significant improvement of sperm number and motility.

Advantageously, the combination according to the present invention is used to rescue $H_2S$ concentration in seminal plasma of subfertile and infertile men and to treat idiopathic male infertility.

The enzyme HO-1, which triggers $H_2S$ release, is also known as heat shock protein 32 being it one of the proteins activated by tissue exposure to stresses, including heating as seen in varicocele. Shiraishi K & Naito K (Human Reproduction 2005; 20(9): 2608-2613) analyzed HO-1 expression from testicular biopsies of varicocele patients and found that the expression of HO-1 in Leydig cells increased with increasing varicocele grade but was inversely correlated with the testicular damage, i.e. HO-1 exerted a protective action. The inventor understands that failure to increase the expression of HO-1 following varicocele is a cause of subsequent infertility. Accordingly, testicular heat exposure in mice causes a fall of the endogenous production of $H_2S$. Moreover, the application of a $H_2S$ donor to testicular germ cell exposed to heat stress abrogated the apoptotic response and improved the mitochondrial bioenergetics. This confirmed by varicocele rat models where the administration of a $H_2S$ donor prevents the testicular damages to a large extent.

Advantageously, the combination according to the present invention is used to rescue $H_2S$ endogenous production in testes and the spermatogenesis of men with varicocele, before or after surgical correction.

The human seminal plasma is known to carry lymphocytes, including Treg type. These Tregs, possibly sperm antigen specific, pass to the women at time of coitus and are supposed to contribute to the generation of immune tolerance to the fetus in the women, thus contributing to implantation, and thereafter to expand during pregnancy to sustain over time such immune tolerance. Accordingly, an improved endogenous release of $H_2S$ may sustain adequate Treg activity in seminal plasma.

Advantageously, the combination according to the present invention is used to improve the Treg activity in men partners to couples suffering repeated implantation failure and/or repeated pregnancy loss.

In a preferred embodiment, the combination according to the present invention is used to treat male infertility, whether or not associated to oligospermia, asthenospermia and teratospermia.

In a preferred embodiment, the combination according to the present invention is used to treat varicocele, before or after surgical repair. In a preferred embodiment, the combination according to the present invention is used to treat men partners to couples suffering repeated implantation failure and/or repeated pregnancy loss.

In a further aspect, the present invention relates to the use of the aforementioned compositions to support the growth and maturation of ovarian oocytes/follicles, embryos and stem cells undergoing to in vitro culture. A main problem encountered with the in vitro culture of ovarian oocytes/follicles, embryos and stem cells is their epigenetic stability and their resistance to oxy-redox imbalances. Indeed, differently from in vivo conditions, in vitro cultures do not enjoy the metabolic support of the whole organism (e.g. liver and kidney functions) and entirely rely for their metabolic needs on the substances included in the culture medium of concern. For a series of technical, biochemical and industrial reasons all of the available culture media do not adequately support the oxy-redox homeostasis, DNA methylation and energy production causing incomplete or defective maturation in the case of oocytes/follicles and embryos and the so-called cell line instability in case of cultures of stem cells. It has been now surprisingly discovered that the composition of the present invention, duly formulated as a ready to use liquid medium at a concentration ranging from 1 in 100 ml to 1 in 2000 ml of the amounts equivalent to a recommended daily human oral dose, is effective in adjusting the oxy-redox balance, in normalizing the epigenetic processes and in boosting the energy output of ovarian oocytes/follicles, embryos and stem cells undergoing in vitro culture.

In a preferred embodiment, the compositions according to the invention can be formulated as a liquid medium used as an add on to any culture medium to improve the oxy-redox balance, the epigenetic processes and the energy output of ovarian oocytes/follicles, embryos and stem cells undergoing in vitro culture.

In a preferred embodiment, the compositions according to the invention can be administered to mammals, particularly to humans. Preferably, the compositions according to the invention can be administered to adults or a pediatric population.

The daily dose and the duration of the treatment vary according to the indication, the age, and the patient's clinical situation.

The following examples are intended to better understand the invention, without in any way limiting it.

EXAMPLES

Example 1

A tablet for oral administration was formulated by including all the targeted nutritional substances as follows: L-Cystine 125 mg; taurine 125 mg; pyridoxal-5-phosphate 5 mg. The excipients included calcium phosphate, magnesium salt of fatty acids, cross-linked carboxymethyl cellulose, and silicon dioxide.

The resulting tablet had a global mass of 520 mg and was of white color, odorless and tasteless. The stability of the tablet was investigated under standard (25° C.±2° C.; 60% R.H.±5%) conditions up to 36 months and under accelerated conditions (40° C.±2° C.; 75% R.H.±5%) up to 9 months. The stability was assessed by monitoring the organoleptic properties, by checking the microbial load and by titration of the nutritional substances. All the results were within the approved range up to the end of the stability program in both the tested conditions.

Example 2

Ten healthy subjects (5 women) aged between 30 and 45 years, non-smokers and with borderline hyperhomocysteinemia assumed the composition formulated according to EXAMPLE 1, 2 tablets in the morning and 2 tablets in the evening. A sample of venous blood was taken in the morning within 9.00 hours after overnight fasting at baseline and after one week of treatment. The metabolites were detected by mass spectrometry or ion chromatography as appropriate. The average homocysteine concentration dropped from 13.8 to 8.3 μMol/L with a 40% reduction. Noteworthy, homocysteine decreased in all subjects, including those starting with a normal value. There were little changes of cysteine (+6%) and GSH (+7%) concentration and of the GSH to GSSG ratio (+14%). In contrast, there was a sharp increase of lanthionine (+83%), indicating increased $H_2S$ generation from CBS, of homolanthionine (+64%), indicating increased $H_2S$ generation from CSE, and of 3-mercaptopyruvate (+54%) and sulfate (+41%), indicating increased $H_2S$ generation from 3MST and increased $H_2S$ oxidation in mitochondria for the generation of ATP. Thus, the combination was very effective in reducing homocysteinemia and the effect was associated to a sharp increase of the release of $H_2S$ and to ATP generation.

Advantageously, the regular assumption of the composition according to the invention may help to restore adequate $H_2S$ release and to reduce blood fasting homocysteine.

Advantageously, the regular assumption of the composition according to the invention may help to correct mitochondrial dysfunction.

Example 3

Five male subjects aged 30-40, following a healthy diet and virtually free from diseases were tested for plasma NADH concentration by enzymatic cycling reaction and for erythrocyte GSH after assuming vitamin C, 2 gr per day during 1 week and, after a 2 week wash out, vitamin C, 2 gr per day, together with the composition formulated according to EXAMPLE 1, 4 tablets per day, for 1 week. Vitamin C caused a subclinical reductive stress as reported by a 40% increase of plasma NADH and 31% and 63% increase of erythrocyte GSH and GSH to GSSG ratio, respectively. The add-on of the composition formulated according to EXAMPLE 1 completely prevented these changes with just 7% increase of NADH, and an as well very small increase of GSH (8%) and GSH to GSSG ratio (17%). Thus, the aforementioned composition prevented the reductive stress induced by a powerful reducing agent.

Advantageously, the composition according to the invention positively modifies the oxy-redox balance and prevents the reductive stress induced by powerful reducing substances.

Example 4

Eight patients (4 women) aged between 40 and 60 years with newly diagnosed insulin resistance were sampled at baseline and after 3 months of treatment with the composition formulated according to EXAMPLE 1, 2 tablets in the morning and 2 tablets in the evening. Insulin resistance estimated as HOMA-IR decreased from 3.1 to 2.5 and glycated hemoglobin (HbA1c) from 7.1 to 6.2, both indicating an improved glucose homeostasis. Malondialdehyde (MDA) was tested by thiobarbituric acid reactive substance assay as an index of lipid oxidative damage and decreased from 328 to 217 indicating a decreased oxidative load. Thus, the composition according to the invention was effective in reducing insulin resistance.

Advantageously, the composition according to the invention decreases the oxidative load allowing the correction of insulin resistance.

Example 5

Bacterial lipopolysaccharide (LPS) is known to induce endothelial dysfunction. Ten adult rabbits were induced endotoxic shock by a single LPS bolus (*Escherichia coli* endotoxin, 0.5 mg/kg iv). Five of the rabbits were pre-treated for 2 weeks by oral gavage of a solution containing the composition formulated according to EXAMPLE 1: 4 tabs dissolved in 100 ml water, daily oral gavage with 3 ml of the achieved solution. One day after LPS injection, untreated rabbits showed increased circulating polynuclear neutrophils and fibrinogen with reduced platelet count, coagulation factors II and V and Protrombin index. The same changes occurred in pre-treated rabbits at a far lower extent indicating a prevention of the coagulopathy from LPS. Two out of 5 non pre-treated rabbits died before day 5 after LPS whereas all pre-treated animals survived up to day 5 post LPS when the animals were sacrificed and aorta segments were collected to check endothelial damage. Endothelial injury was present on 31% of the tested area of control rats whereas injuries did not exceed 5% in pre-treated animals.

Advantageously, the composition according to the invention prevents the endothelial dysfunction induced by bacterial LPS.

Example 6

Twenty male subjects with newly diagnosed arterial hypertension and with a diastolic blood pressure>90 mmHg and a systolic blood pressure>130 mmHG assumed the composition formulated according to EXAMPLE 1, 4 tablets per day, for 2 weeks. Blood pressure was measured by mercury sphygmomanometer according to the standard clinical practice at baseline, at the end of the 2-week treatment and after a further week of wash-out. After treatment, the average diastolic blood pressure decreased from 93.25 to 87.8 mm Hg (−5.45) and the average systolic blood pressure decreased from 134.05 to 125.75 mm Hg (−8.3). Diastolic and systolic blood pressure returned to baseline values (respectively 92.75 and 132.85 mmHg) after one-week wash-out.

Advantageously, the composition according to the invention decreases blood pressure in hypertensive subjects.

Example 7

Twenty Balb/c mice were intranasally infected with $10^7$ pfu of Respiratory Syncytial Virus (RSV) grown in and purified from Hep-2 cells. Ten mice were pre-treated for 1-week pre-infection and 1-week post-infection by oral gavage of a solution containing the composition formulated according to EXAMPLE 1: 2 tabs dissolved in 50 ml water, daily oral gavage with 1 ml of the achieved solution. The other ten infected mice served as controls. The loss of body weight following infection and the viral-induced illness score were recorded. On day 3 post-infection the weight loss in treated animals was 8.4% compared to 18.8% in untreated animals The average illness score was, respectively for treated and untreated animals 1.1 vs 2.3 at day 1; 1.3 vs 2.95 at day 2; 0.25 vs 3.3 at day 3; 0 vs 0.9 at day 4. All animals were symptom free at day 5. Thus, the treatment was effective in reducing the burden of RSV infection in mice.

Advantageously, the composition according to the invention can be used to treat respiratory viral infections.

Example 8

An animal model of Ventilation Induced Lung Injury (VILI) was established by exposing 10 anesthetized rats to 4-hour mechanical ventilation at tidal volume of 30 mL/kg, respiratory rate of 50/min, inspiratory/expiratory ratio of 1:1, and FiO2 of 50%. Five of the rats were pre-treated during one week by oral gavage of a solution containing the composition formulated according to EXAMPLE 1: 4 tabs dissolved in 100 ml water, daily oral gavage with 1 ml of the achieved solution. The animals were sacrificed at the end of the exposure to calculate the lung injury score (from 0, no injury, to 4, more than 75% injured) and the edema rate by the lung wet-to-dry ratio. Untreated animals had a lung injury score of 3.75 and a lung wet-to-dry ratio of 7.5 compared to, respectively, 1.9 and 3.8 in pre-treated animals indicating that the treatment had prevented the lung injury to a large extent.

Advantageously, the composition according to the invention can be used to prevent VILI.

Example 9

The transgenic 3×Tg-AD mice overexpress human amyloid precursor protein (APP), PS1 and tau protein and develop severe Alzheimer's disease. Ten, 6-month old 3×Tg-AD mice were treated during 12 weeks (up to the age of 9 months) by oral daily gavage of a solution containing the composition formulated according to EXAMPLE 1: 2 tabs dissolved in 50 ml water, daily oral gavage with 1 ml of the achieved solution. Other 10, 6-month old mice did not receive the treatment and served as controls. By the age of 9 months treated mice, as compared to untreated animals, showed improved cognitive function with respect to the Morris water maze test (escape latency, target zone and target crosses). One animal from each group was sacrificed and target cortex areas were analyzed to calculate the amyloid beta plaque extent: the untreated animal showed extensive amyloid deposition, which was barely detectable in the treated mouse.

Advantageously, the composition according to the invention exerts its activity also within the central nervous system. Advantageously, the composition according to the invention may be used for the treatment and prevention of neurodegenerative diseases linked to lack of $H_2S$ including, but not limited to, Alzheimer's disease and Parkinson's disease.

Example 10

Five patients suffering from psoriasis vulgaris at progressive stage assumed the composition formulated according to EXAMPLE 1, 4 tablets per day, for 2 weeks. At the end of the treatment a sample of blood was taken from these patients and from other 5 age and disease stage matched psoriasis patients to isolate Treg and Tresp lymphocytes. Isolated cells were tested for both the Treg ability to suppress the Tresp proliferation (as triggered by IL-2 and anti-CD28) and the ability to proliferate of Tregs (CSFE labelling). More than 50% of the Tresp from untreated patients proliferated in spite of the expected Treg inhibition whereas only 32% of the Tresp from treated patients proliferated. Opposite, about 45% of the Tregs from treated patients was able to proliferate of compared to less than 30% of those from untreated patients.

Advantageously, the composition according to the invention exerts the ability to boost Treg lymphocyte function in humans. Advantageously, the composition according to the invention can be used for the treatment of autoimmune diseases.

Example 11

C57BL/6 HO-1 knock-out mice do not express HO-1 and are unable to generate alive offspring due to lack of placentation. Female and male C57BL/6 HO-1 heterozygote knock-out mice (HO-1$^{-/+}$) were cross-breed and their offspring was investigated. The females of 10 mice couples were treated during 2 weeks before mating by oral daily gavage of a solution containing the composition formulated according to EXAMPLE 1: 2 tabs dissolved in 50 ml water, daily oral gavage with 1 ml of the achieved solution. Their offspring was compared to that from other 10 untreated mice couples. Pre-treated couples produced an average of 6.5 pups/litter, whereas untreated couples produce just 4.1 pups/litter. Moreover, the birth weight of pups from untreated mice couple was about 30% lower than that from treated couples. In summary, the treatment prevented the low reproductive efficiency and placentation of genetically weak animals and is expected to do the same in human pregnancies.

Advantageously, the composition according to the invention exerts the ability to resume low efficient placentation from lack of HO-1/CO/$H_2S$ activation. Advantageously, the composition according to the invention can be used for the treatment of recurrent implantation failure and recurrent miscarriage.

Example 12

Couples referring to an assisted reproduction clinic and put on the waiting list were offered a nutritional supplementation for both partners with the composition formulated according to EXAMPLE 1, 4 tablets per day, as a preparation for the treatment. Matched couples refusing the supplementation served as controls. A total of 24 couples started the supplementation and were observed for an average of 3.2 months whereas 21 couples serving as controls were followed up for an average of 2.9 months. Nine out of 24 treated couples (37.5%) experienced a spontaneous pregnancy during the waiting time compared to 1 out of 21 (5%) in the control group.

Advantageously, the composition according to the invention can be used for the treatment of couple's infertility.

Example 13

Ten couples with more than 2 previous Assisted Reproductive Technologies (ART) failures were offered a nutritional supplementation for both partners with the composition formulated according to EXAMPLE 1, 4 tablets per day, during 3 months in preparation of a new ART cycle and thereafter during the hormonal stimulation. Other ten couples with the same characteristics and refusing the supplementation were observed for a similar period before a new ART attempt and served as controls. After the new ART cycle, 7 out of 10 pre-treated couples achieved a clinical pregnancy compared to 2 of 10 couples in the control group.

Advantageously, the composition according to the invention can be used for the treatment of couple's infertility within ART programs.

Example 14

Surgical varicocele was induced in 20 adult male Wistar rats. Two months post-surgery a significant damage to testis and sperm cells was confirmed and 10 of the varicocele rats received a treatment with the composition formulated according to EXAMPLE 1, 4 tabs dissolved in 100 ml water, daily oral gavage with 1 ml of the achieved solution, the other 10 rats served as controls. Two months later, i.e. 4 months after surgery, untreated rats had oligospermia, asthenospermia and increased lipid peroxidation whereas treated rats had only minor decrease of sperm number and quality and lipid peroxidation had returned close to baseline. Six months later, i.e. 8 months after surgery, the rat testes of untreated rats showed intensive iron deposition in germinal cells and interstitial space indicating a defective activity of HO-1 with release of ferric iron within the tissues. Due to the oxidative damage caused by iron accumulation the spermatogenesis was unlikely to be restored in these animals. Treated rats presented only very minor iron staining in parallel with their preserved spermatogenesis.

Advantageously, the composition according to the invention prevents HO-1 inactivation and testicular iron deposition in varicocele. Advantageously, the composition according to the invention can be used to treat human varicocele.

Example 15

Bovine cumulus-oocyte complexes (COC) were obtained from the ovaries of slaughtered cows. COCs were aspirated from antral follicles (3-8 mm in diameter) and oocytes with at least four layers of cumulus cells with homogenous cytoplasm were selected. A sample of COCs was used to check the nuclear maturation stage at time of sampling (n=20). Control COCs (Group 1) were matured in vitro using 500 µL of TCM199 medium (Gibco; Invitrogen Co., Grand Island, NY, USA) supplemented with FSH and hCG and with 10% (v:v) calf serum (N=20). Sibling bovine COC (n=20) were cultured with the same medium further supplemented with 100 µL of a solution containing the composition formulated according to EXAMPLE 1 where the amount of substances equivalent to a daily human dose had been diluted in 1 L (Group 2). Out of 20 COCs tested at time of sampling, 15 were at GV stage, 5 at intermediate stage and none was at MII stage. The development of the oocytes was assessed after 24 hours of in vitro culture: Group 1 produced 4 GV, 5 intermediate and 11 MII stage (matured) oocytes; Group 2 produced 2 GV, 3 intermediate and 15 MII oocytes (+20% vs Group 1) indicating that the addition of the composition formulated according to EXAMPLE 1 had improved the maturation rate. After in vitro fertilization of the MII oocytes obtained from the previous experiment blastocyst formation rate was 4/11 (36%) in Group 1, which improved to 9/15 (60%) in Group 2.

Advantageously, the in vitro supplementation of the culture medium with a solution containing the composition listed in EXAMPLE 1 results in an increased rate of in vitro maturation of ex-vivo oocytes and in a higher rate of blastocyst development. The composition according to the present invention may improve the efficiency of the in vitro culture of oocytes, embryos and stem cells.

The invention claimed is:

1. A combination comprising:
   a) L-cystine in amounts ranging from 40 to 60% by weight;
   b) taurine and/or the pharmaceutically acceptable salts thereof in amounts ranging from 40 to 60% by weight;
   c) pyridoxal-5-phosphate and/or the pharmaceutically acceptable salts thereof in amounts ranging from 0.1 to 5% by weight;
   wherein said the percentages are with respect to the sum of components a), b) and c).

2. A composition comprising the combination according to claim 1 and at least one physiologically acceptable excipient.

3. The composition according to claim 2, wherein the physiologically acceptable excipient is selected from the group consisting of bulking agents, anticaking agents, stabilizers and a mixture thereof.

4. The composition according to claim 2, characterized in being in the form of tablet, capsule, granule, soluble granule, drinkable solution, lavage solution, breathable solution, injection or suppository.

5. The combination according to claim 1, wherein the L-cystine is in amounts ranging from 45 to 55%; taurine is in amounts ranging from 45 to 55%; and pyridoxal-5-phosphate is in amounts ranging from 1 to 3%.

* * * * *